(12) United States Patent
Pettit et al.

(10) Patent No.: US 7,439,265 B2
(45) Date of Patent: Oct. 21, 2008

(54) IRCINIASTATINS A AND B

(75) Inventors: George R. Pettit, Paradise Valley, AZ (US); Jun-Ping Xu, Chandler, AZ (US)

(73) Assignee: Arizona Board of Regents, a body corporate of the State of Arizona, acting for and on behalf of Arizona State University, Scottsdale, AZ (US)

( * ) Notice: Subject to any disclaimer, the term of this patent is extended or adjusted under 35 U.S.C. 154(b) by 42 days.

(21) Appl. No.: 10/580,572

(22) PCT Filed: Nov. 17, 2004

(86) PCT No.: PCT/US2004/038530

§ 371 (c)(1),
(2), (4) Date: May 24, 2006

(87) PCT Pub. No.: WO2005/054809

PCT Pub. Date: Jun. 16, 2005

(65) Prior Publication Data

US 2007/0135516 A1      Jun. 14, 2007

Related U.S. Application Data

(60) Provisional application No. 60/525,565, filed on Nov. 25, 2003.

(51) Int. Cl.
*A61K 31/35* (2006.01)
*C07D 311/76* (2006.01)

(52) U.S. Cl. ...................... 514/456; 549/289

(58) Field of Classification Search ............. 549/289; 514/456

See application file for complete search history.

(56) References Cited

U.S. PATENT DOCUMENTS

2007/0015821 A1    1/2007   Brabander et al. .......... 514/457

OTHER PUBLICATIONS

De Brabander et al., "Improved Synthesis of the C17-C25 Fragment of the Anti-Tumor Natural Product Psymberin/Irciniastatin A", 231st ACS National Meeting, Atlanta, GA, Mar. 26-30, 2006 (Abstract only).

Jiang et al., "Synthesis and Complete Stereochemical Assignment of Psymberin/Irciniastatin A", *Journal of the American Chemical Society*, 127(32):11254-11255 (2005).
Pettit et al., "Antineoplastic Agents. 520. Isolation and Structure of Irciniastatins A and B from the Indo-Pacific Marine Sponge *Ircinia ramosa*", *J. Med. Chem.*, 47:1149-1152 (2004).
Piel et al., "Exploring the Chemistry of Uncultivated Bacterial Symbionts: Antitumor Polyketides of the Pederin Family", *J. Nat. Prod.*, 68:472-479 (2005).
Shangguan et al., "A Formal Synthesis of Psymberin", *Organic Letters*, 9(6):1093-1096 (2007).
Williams, Lawrence J., "Psymberin (irciniastatin A) via spirodiepoxide", 38th Middle Atlantic Regional Meeting of the American Chemical Society, Hershey, PA, Jun. 4-7, 2006 (Abstract only).
International Search Report for PCT/US04/38503 dated Jun. 3, 2005.
Written Opinion of the International Search Authority for PCT/US04/38503 dated Jun. 3, 2005.
Cichewicz et al, "Psymberin, A Potent Sponge-Derived Cytotoxin from *Psammocinia* Distantly Related to the Pederin Family", Organic Letters, vol. 6, No. 12, pp. 1951-1954, 2004.

*Primary Examiner*—Bernard Dentz
(74) *Attorney, Agent, or Firm*—Fennemore Craig, P.C.

(57) ABSTRACT

The Indo-Pacific marine sponge Ircinia ramosa has been found to contain two powerful (GI50 0.001 to <0.0001 μg/ml) murine and human cancer cell growth inhibitors, denominated herein as irciniastatin A and irciniastatin B. Both were isolated (10-3 to 10-4% yields) by cancer cell line bioassay-guided techniques and named irciniastatins A (1) and B (2). Structural elucidation by a combination of spectral analyses, primarily high resolution mass and 2D-NMR (principally APT, HMQC, HMBC and ROESY) revealed unusual structures 1 and 2.

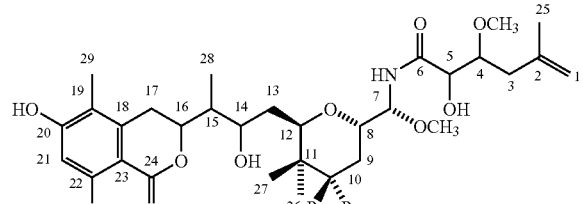

1, R = OH, R₁ = H, Irciniastatin A
2, R, R₁ = O, Irciniastatin B

8 Claims, 1 Drawing Sheet

1, R = OH, R₁ = H, Irciniastatin A
2, R, R₁ = O, Irciniastatin B

US 7,439,265 B2

IRCINIASTATINS A AND B

RELATED APPLICATION DATA

This application is the U.S. national stage of PCT/US04/38530 filed on Nov. 17, 2004, which is based on and claims the benefit of U.S. Provisional Patent Application No. 60/525,565 filed on Nov. 25, 2003, the disclosure of which is incorporated herein in its entirety by this reference.

Financial assistance for this invention was provided by the United States Government, National Institutes of Health Grant Numbers CA44344-01-12 and RO1 CA90441-01-02, the Arizona Disease Research Commission, and numerous private contributors. Thus, the United States Government has certain rights in this invention.

FIELD OF THE INVENTION

This invention relates to novel, naturally-derived compounds having anticancer properties.

BACKGROUND OF THE INVENTION

Numerous marine organism-derived anticancer drugs are either already in human cancer clinical trials or advancing in preclinical development toward that vitally important objective. Others are in earlier stages of development. Described herein are novel anticancer drug candidates based on a marine organism, the marine sponge *Ircinia ramosa*. (Pettit, G. R., et al., Biosynthetic products for anticancer drug design and treatment: the bryostatins, *In Anticancer Drug Design*, Ed. by B. Baguley, Academic Press, San Diego, Calif., 2002, pp. 203-235; Clamp, A., et al., The clinical development of the bryostatins, *Anti-Cancer Drugs* 2002, 13, 673-683; O'Brien, M. et al., Synthesis of the C(1)-C(16) fragment of bryostatins, *Tetrahedron Lett.* 2002, 43, 5491-5494; Saad, E. D., et al., Phase II study of dolastatin 10 as first-line treatment for advanced colorectal cancer, *Am. J Clin. Oncol.* 2002, 25, 451-453; van Kesteren, C., et al., Clinical pharmacology of the novel marine-derived anticancer agent Ecteinascidin 743 administered as a 1- and 3-h infusion in a phase I study, *Anti-Cancer Drugs* 2002, 13, 381-393; Endo, A., et al., Total synthesis of Ecteinascidin 743, *J Amer. Chem. Soc.* 2002, 124, 6552-6554; Jimeno, J. M., A clinical armamentarium of marine-derived anticancer compounds, *Anti-Cancer Drugs* 2002, 13, S15-S19; Paterson, I., et al., Total synthesis of altohyrtin A (spongistatin 1): an alternative synthesis of the CD-spiroacetal subunit, *Tetrahedron Lea.* 2002, 43, 3285-3289; Crimmins, M. T., et al., Asymmetric total synthesis of spongistatins 1 and 2, *J. Amer. Chem. Soc.* 2002, 124, 5661-5663; Cragg, G. M., et al., Medicinals for the millennia. *Ann. New York Acad. Sci.* 2001, 953, 3-25; Vedejs, E., et al., A total synthesis of (−)-Hemiasterlin using N-Bts methodology; *J. Org. Chem.* 2001, 66, 7355-7364; Faulkner, D. J., Marine natural products, *Nat. Prod. Rep.* 2001, 18, 1-49, Faulkner, D. J., Marine natural products. *Nat. Prod. Rep.* 2000, 17, 7-55.)

In the sponge phylum Porifera, the order Dictyoceratida contains very productive families in terms of biologically active constituents and *Ircinia ramosa* is a member of one, the Ircinidae family. The *Ircinia* genus is known in the Indo-Pacific area including Malaysia, Semporna, Borneo and Papua New Guinea (Gosliner, T. M., et al., Coral Reef Animals of the Indo-Pacific, *In Sea Challengers*, Monterey, Calif., p. 25, 1996; Colin, P. L., et al., *Tropical Pacific Invertebrates*, Coral Reef Research Foundation, p. 53, 1995.

SUMMARY OF THE INVENTION

The present invention relates to novel compounds, useful in the treatment of cancer. The novel compounds are derived from marine organisms, in particular from the marine sponge *Ircinia ramosa*, and exhibit valuable anti-cancer properties. The compounds are denominated as irciniastatin A and irciniastatin B. Structural elucidation revealed the unusual structures of these compounds.

Irciniastatins A and B appear to be powerful ($GI_{50}$ 0.001 to <0.0001 μg/ml) murine and human cancer cell growth inhibitors. Both were isolated ($10^{-3}$ to $10^{-4}$% yields) by cancer cell line bioassay-guided techniques. The dichloromethane-methanol extract exhibited strong ($GI_{50}$ $10^{-2}$ μg/ml) activity against the P388 lymphocytic leukemia and a minipanel of human cancer cell lines, including pancreas, breast, CNS, lung, colon and prostate cell lines.

DETAILED DESCRIPTION OF THE INVENTION

Figure 1:
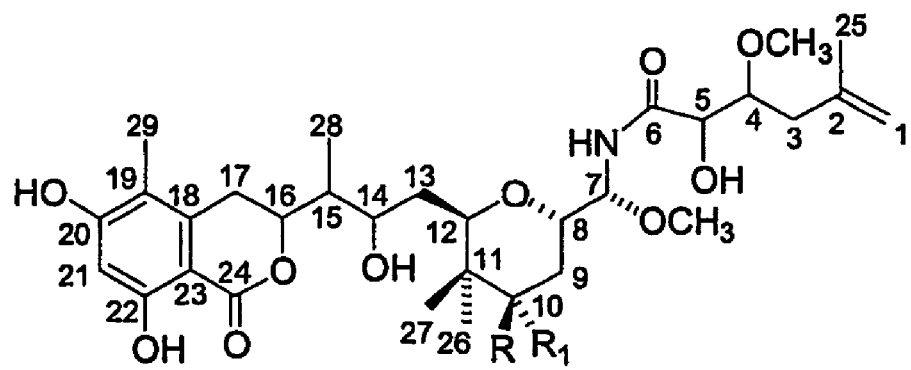
FIG. 1 illustrates the structures of irciniastins A and B.

An encouraging number of marine organism-derived anticancer drugs are either already in human cancer clinical trials or advancing in preclinical development toward that vitally important objective. Others are in earlier stages of development. The present invention is a result of the inventors' efforts to discover increasingly useful anticancer drug candidates based on marine organism constituents. In particular, the inventors have discovered a promising lead offered by the marine sponge Ircinia ramosa. In the sponge phylum Porifera, the order Dictyoceratida contains very productive families in terms of biologically active constituents and *Ircinia ramosa* is a member of one, the Ircinidae family. The *Ircinia* genus is known in the Indo-Pacific area including Malaysia, Semporna, Borneo and Papua New Guinea.

The following describes how the compounds of interest, Irciniastatins A and B, were obtained. These compounds are quite remarkable in terms of both cancer cell growth inhibition and novel structure. Since 1972, the *Ircinia* genus has been part of over 135 published studies where some eleven have led to cancer cell growth inhibitors such as the marine alkaloid irciniamine. (Kuramoto, M., et al., a novel cytotoxic alkaloid from *Ircinia* sp., *Chem. Lett.* 2002, 4, 464-465; Salama, A. M., et al., Antimicrobial and antitumor activity of variabiline and its enanthiomers isolated from *Ircinia felix; Revista Colombiana de Ciencias Quimico-Farmaceuticas* 2001, 30, 74-80; Yan, S-J., et al. Rare long conjugated diterpene ketene from the marine sponge *Ircinia selaginea* (Lamark), *Gaodeng Xuexiao Huaxue Xuebao* 2001, 22, 949-951; Takada, N., et al., Isolation and structures of haterumalides NA, NB, NC, ND, and NE, novel macrolides from an Okinawan sponge *Ircinia* sp., *Tetrahedron Lett.* 1999, 40, 6309-6312; Prokofeva, N. G., et al., T. A. Membranotropic effects of cyclic lipopeptides produced by a marine isolate of the bacteria *Bacillus pumilus, Biologiya Morya* (Vladivostok) 1996, 22, 179-182; Mau, C. M. S., et al., a cyclic hexapeptide from the sponge *Ircinia dendroides, J. Org. Chem.* 1996, 61, 6302-6304; Kondo, K., et al., Structures of ircinals A and B, novel alkaloids from the Okinawan marine sponge *Ircinia* sp., *Tennen Yuki Kagobutsu Toronkai Koen Yoshishu* 1992, 34, 463-469; Kamimura, D., et al., Novel antitumor sesterterpenoids, *Jpn. Kokai Tokkyo Koho* 1993, JP 92-40445 19920131; Kondo, K., et al., Ircinals A and B from the Okinawan marine sponge *Ircinia* sp.: Plausible biogenetic precursors of manzamine alkaloids, *J. Org. Chem.* 1992, 57, 2480-2483; Mihopoulos, N., et al., *Ircinia spinosula*.

Zeitschrift fur Naturforschung. Section C. Journal of Biosciences 1999, 54, 417423; De Rosa, S., et al., Biological effects of prenylated hydroquinones: Structure-activity relationship studies in antimicrobial, brine shrimp, and fish lethality assays, *J. Nat. Prod.* 1994, 57, 1711-1716.)

The sponge was preserved in methanol and extracted with dichloromethane-methanol (1:1). The dichloromethane fraction was subjected to solvent partition separation (n-hexane and 9:1 $CH_3OH$-water followed by $CH_2Cl_2$ and 3:2 $CH_3OH$— water). The resulting dichloromethane-soluble fraction was separated, guided by P388 leukemia cell line bioassay, employing gel permeation and partition column chromatographic procedures on Sephadex LH-20 with $CH_3OH$, $CH_2Cl_2$—$CH_3OH$ (3:2), and n-hexane-$CH_2Cl_2$—$CH_3OH$ (5:1:1) as eluents. Final separation and purification procedures were performed by utilizing reversed phase (C18) HPLC (30% and 38% $CH_3CN$ in $H_2O$) to yield the most potent constituents irciniastatins A (1) and B (2), 34.7 mg and 2.2 mg, respectively. The dichloromethane-methanol extract gave strong ($GI_{50}$ $10^{-2}$ μg/ml) activity against the P388 lymphocytic leukemia and a minipanel of human cancer cell lines.

Irciniastatins A (1) and B (2) were obtained as colorless amorphous powders. The high resolution FAB mass spectrum of 1 showed a pseudomolecular ion peak at m/z 610.3228 $[M+H]^+$, which revealed the molecular formula as $C_{31}H_{48}NO_{11}$ (calc. 610.3228) and implying nine degrees of unsaturation. Both 1 and 2 exhibited similar resonance patterns in their $^1H$ and $^{13}C$ NMR spectra.

Interpretation of 2D-COSY, TOCSY and HMQC spectra of irciniastatin A (1) revealed three spin-spin systems (I: $CH_2$=$CH(CH_3)$—$CH_2$—$CH(OCH_3)CH(OH)$—CO—, II: NH—$CH(OCH_3)$—CH(O—)—$CH_2$—CH(OH)—, and III: CH(O—)—$CH_2$—CH(OH)—$CH(CH_3)$—CH(O—)—$CH_2$—). A methyl, a carbonyl and six aromatic carbons remained and were deduced to be a 1'-carbonyl-2',4'-dihydroxyl-5'-methylbenzene unit based upon HMBC correlations (Table 1). One proton on the benzene ring had a quite low downfield chemical shift (δ 11.13 s), which indicated that the proton was hydrogen bonded with an adjacent carbonyl oxygen atom. An HMBC correlation from the NH (δ 7.09 d) to a carbonyl carbon (δ 173.49 s) defined an amide linkage between spin-spin systems I and II. A series of HMBC correlations around spin-spin system II and III as well as one quaternary carbon (δ 38.75 s) and two geminal methyl groups (δ 0.92 s/13.67 q and δ 0.97/23.06 q), cross peaks of H-8/C-12, H-12/C-8, H-12/C-10, H-10/C-12 and H-9/C-11 (Table 1), established a gem-dimethyl-tetrahydropyran unit between spin-spin systems II and III. Between spin-spin system III and the benzene ring, many HMBC correlations were observed, namely from H-17 (δ 2.82 and 2.89) to C-18 (δ 139.68 s), C-19 (δ 113.20 s) and C-23 (δ 101.59 s), from H-16 (δ 4.53) to C-18, and from methyl protons at the benzene ring (C-29, δ 2.02 s) to C-17 (δ 28.39 t). Thus, connection of one side of spin-spin system III with the 1'-carbonyl-2',4'-dihydroxyl-5'-methylbenzene portion was confirmed. Also, according to HMBC cross peaks two methoxyl groups (δ 3.38 s) were identified and linked at C-4 (δ 80.53 d) and C-7 (δ 78.31 d), respectively.

The $^{13}C$ chemical shifts of C-5 (δ 73.11 d), C-10 (δ 71.41 d) and C-14 (δ 73.75 d) indicated the presence of a hydroxyl group linked to each of the three carbons. A special deuterated solvent ($CD_3OH$) was used in 1D and 2D-NMR experiments for defining each hydroxyl group location. Four active hydroxyl protons were determined to be located at C-5, C-14, C-20 and C-22. Since a few signals were found to overlap with the large $D_2O$ resonance, the hydroxyl proton at C-10 was not observed. Comparison of the $^{13}C$ chemical shift of C-16 with those of C-5, C-10, and C-14 showed that C-16 was shifted downfield by 5.66 to 8.0 ppm. That data clearly showed C-16 was the site of another ring involving an oxygen atom that satisfied the last one degree of unsaturation. In NMR experiments employing $CD_3OH$ solvent, the lactone carbonyl group (C-14, 6 170.44 s) was found linked to the benzene ring, which suggested the formation of a six-member lactone with C-16. Based upon the above extensive analysis, the structure of irciniastatin A (1) was established.

Figure 2:
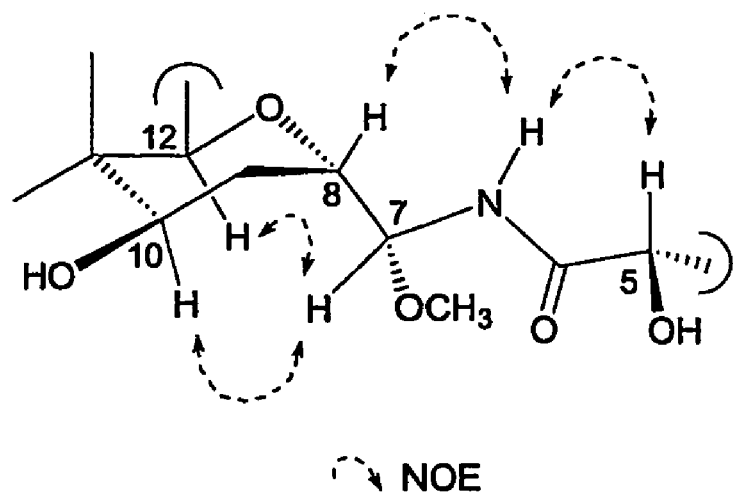
FIG. 2 illustrates the NOE correlations around C-5-C-12 in irciniastatin A.

A review of 2D-NOESY and ROESY experiments afforded valuable stereochemical information for assignment of four chiral centers. Because both protons at C-5 and C-8 exhibited NOE correlations with the amide proton (NH), these three protons were clearly oriented from the same side in space (see FIG. 2). Two other NOE correlations were observed from H-7 to the two axial protons on the tetrahydropyran, H-10 and H-12, and implied that these three protons were in close proximity on another side. Therefore, the relative configuration of the four chiral carbons were deduced as 7R*, 8S*, 10R* and 12R*.

Irciniastatin B (2) was found to correspond to molecular formula $C_{31}H_{45}NO_{11}$, as determined by high resolution FAB mass spectroscopy indicating two hydrogens less and one degree of unsaturation more than irciniastatin A (1). In the $^{13}C$-NMR spectrum one hydroxyl disappeared and one ketone carbon signal (δ 210.00 s) appeared compared to that of 1. HMBC correlations from H-8, H-9, H-12 and two geminal methyl (C-12 and C-27) to the ketone carbon were observed, suggesting the ketone was at C-10. Also, the chemical shifts of two neighboring carbons (C-9 and C-11) were shifted downfield by 8.88 ppm and 10.65 ppm, respectively. The resonance shifts supported the assignment from the HMBC experiment. Therefore, irciniastatin B was assigned structure 2. Both irciniastatins A and B resisted a variety of attempts at crystallization, and that has so far precluded completing the stereochemical assignments by X-ray crystal structure determination. Synthetic approaches to these important new anticancer drug candidates will now be undertaken to define the remaining chiral centers and increase the availability of both irciniastatins and derivatives for further development.

Irciniastatins A (1) and B (2) displayed powerful cancer cell growth inhibition against the murine P388 leukemia cell line and six human cancer cell lines with $GI_{50}$ values of $10^{-3}$-$10^{-4}$ μg/ml (Table 2). Although there was only one minor difference at C-10 between irciniastatins A and B, the cell growth inhibition of 2 proved to be ten times stronger than that of 1 against the murine P388 leukemia, human pancreas (BXPC-3), breast (MCF-7) and CNS (SF268) cancer cell lines. However, against lung cancer cells (NCI-H460), irciniastatin A was at least 10 times more active than irciniastatin B. Irciniastatin A (1) was available in sufficient quantity to evaluate possible antimicrobial activity. Irciniastatin A (1) had marginal antifungal and antibacterial activities, with minimum inhibitory concentrations of 16 μg/ml for *Cryptococcus neoformans* and 64 μg/ml for *Neisseria gonorrhoeae*.

Irciniastatins A (1) and B (2) are extremely promising anticancer agents and their development, including synthetic approaches and investigation of possible microorganism sources, is in progress.

EXPERIMENTAL

General Procedures.

Organic solvents used for column chromatography were freshly distilled. Sephadex LH-20, particle size 25-100 μm, used in gel permeation and partition column chromatographic separations was obtained from Pharmacia Fine Chemicals AB, Uppsala, Sweden. The TLC plates were viewed under shortwave UV light and then developed by 20% $H_2SO_4$ or 3% ceric sulfate—3N sulfuric acid spray reagent following by heating at approximately 150° C. For HPLC separations, a Phenomenex Zorbox SB C18 particle size 10μ, Φ 9.4 mm×25 cm) C18 column and a Phenomenex IB-SIL (particle size 5μ, Φ 4.6 mm×25 cm) C-18 column were used in reversed-phase mode with Waters Delta (model 600) solvent metering pumps in conjunction with Waters 2487 Dual λ Absorbance Detector (at λ 254 nm), with Gilson (model 306) solvent metering pumps and Gilson 118 UV/VIS detection at λ 254 nm. HPLC grade organic solvents were purchased from EM Science and pure water was produced by Barnstead Easypure PF compact ultrapure water system model D7031. The solvent partitioning sequence was a modification of the original procedure of Bligh and Dyer. (Bligh, E. G., et al., A rapid method of total lipid extraction and purification, *Can. J. Biochem. Physiol.* 1959, 37, 912.)

Optical rotation was determined employing a Perkin-Elmer Model 241 polarimeter. The UW spectrum was recorded with a Hewlett-Packard 8450 UV-VIS spectrometer. The HRFABMS was measured with a JEOL JMS-LC mate LCMS system. The $^1H$ and $^{13}C$-NMR, APT, $^1H$-$^1H$-COSY, TOCSY (mixing time of 45 msec and 60 msec), HMQC (optimized for $^1J_{H-C}$, =8.2 Hz), ROESY (mixing time of 100 msec and 150 msec) and 2D J-resolution data were recorded using a Varian VXR-500 instrument in $CDCl_3$.

Collection of *Ircinia ramose*

On July 6, 1991 an approximate 1 kg sample of wet *Ircinia cf. ramosa* Bergquist, 1965 (Demospongiae: *Dictyoceratida: Ircinidae*) was collected using SCUBA at −20 to −36 M on a barrier reef near Semporna, Sabah (Borneo), Malaysia. The reddish brown (darkens on exposure to air) encrusting (with vertical branching) sponge with a light brown exterior was preserved in methyl alcohol. Reference specimens are maintained at ASU-CRI and Queensland Museum in Australia.

Extraction and Solvent Partitioning.

The *I. ramosa* sponge sample (~1 kg wet wt) was extracted with methylene chloride-methanol (1:1) and was dried to a 98.8 g residue. This material was successively partitioned using the system MeOH—$H_2O$ (9:1 and 3:2) against n-hexane and methylene chloride, respectively, to yield the most bioactive methylene chloride fraction (1.78 g, yield 1.8%) with $ED_{50}$ 0.0077 μg/ml for P388 and $GI_{50}$ values of 0.0018, <0.001, 0.00089, <0.001, 0.0014 and 0.0012 μg/ml for BXPC-3, MCF-7, SF268, NCI-H460, KM20L2 and DU-145 cells, respectively.

Isolation of Irciniastatins A (1) and B (2).

Two bioactive fractions were obtained from the methylene chloride fraction (1.78 g) by a series of Sephadex LH-20 gel permeation and partition column chromatographic steps using methanol, methylene chloride-methanol (3:2), n-hexane-methylene chloride-methanol (5:1:1) as eluents. Further separation of the two fractions (A: 144 mg and B: 69.5 mg) was performed employing C18 (10μ) reversed-phase column (9.4 mm×25 cm) HPLC with mobile phases 3:7 and 19:31, $CH_3CN$—$H_2O$ to isolate and collect two major peaks. Final purification was achieved by using ODS (5μ) column (4.6 mm×25 cm) HPLC techniques with 3:7 and 19:31 $CH_3CN$—$H_2O$ as eluents. By this means, pure irciniastatins A (34.7 mg, yield $3.51 \times 10^{-3}$%) and B (2.2 mg, yield $2.23 \times 10^{-4}$%) were isolated. Irciniastatin A (1) was obtained as a colorless amorphous powder: $[\alpha]_D$ +24.40° (c, 0.55, $CH_3OH$); UV ($CH_3OH$—$H_2O$) λ 310, 270, 230(sh), 215 nm; FAB-MS m/z 610 [M+H]; HRFABMS m/z 610.3228, $C_{31}H_{48}NO_{11}$ (calc. 610.3228). The $^1H$, APT, HMQC, HMBC, and ROESY (in $CDCl_3$) assignments have been summarized in Table 1.

Irciniastatin B (2) was isolated as a colorless amorphous powder: $[\alpha]_D$ −4.67° (c, 0.15, $CH_3OH$); UV ($CH_3OH$—$H_2O$) λ 310, 270, 230(sh), 215 nm; FAB-MS m/z 608 [M+H]+; HRFABMS m/z 608.3101, $C_{31}H_{46}NO_{11}$ (calc. 608.3071). Refer to Table 1 for the $^1H$, APT, HMQC, HMBC, and ROESY (in $CDCl_3$) data.

Cancer Cell Line Procedures

Inhibition of human cancer cell growth was assessed using the National Cancer Institute's standard sulforhodamine B assay as previously described. Briefly, cells in a 5% fetal bovine serum/RPMI1640 medium solution were inoculated in 96-well plates and incubated for 24 hours Serial dilutions of the compounds were then added. After 48 hours, the plates were fixed with trichloroacetic acid, stained with sulforhodamine B and read with an automated microplate reader. A growth inhibition of 50% ($GI_{50}$ of the drug concentration causing a 50% reduction in the net protein increase) was calculated from optical density data with Immunosoft software. Inhibition of the mouse leukemia P388 cells was assessed in a 10% horse serum/Fisher medium solution for 24 hours, followed by a 48 hour incubation with serial dilutions of the compounds. Cell growth inhibition ($ED_{50}$) was then calculated using a Z1 Beckman/Coulter particle counter. (Monks, A., et al., Feasibility of high-flux anticancer screen using a diverse panel of cultured human tumor cell lines, *J Natl. Cancer Inst.* 1991, 83, 757-766.)

HUVEC and Tube Formation.

Unpolymerized Matrigel (Becton Dickinson) was used to coat the wells (250 μL/well) of a 24-well tissue culture plate and allowed to polymerize for 1 hour at 37° C. HUVEC (human umbilical vascular endothelial cells) (BD Biosciences Clontech) were plated ($6 \times 10^4$ cells/well) in 0.5 mL of EGM-2 complete medium (Clonetics-Bio-Whittaker Cambrex) to which irciniastatin A doses were added in experimental wells. After ~24 hours of incubation, digital photographs were taken.

Antimicrobial Susceptibility Testing.

Ircinastatin A (1) was evaluated against the bacteria *Stenotrophomonas maltophilia* ATCC 13637, *Micrococcus luteus Presque Isle* 456, *Staphylococcus aureus* ATCC 29213, *Escherichia coli* ATCC 25922, *Enterobacter cloacae* ATCC 13047, *Enterococcus faecalis* ATCC 29212, *Streptococcus pneumoniae* ATCC 6303 and *Neisseria gonorrhoeae* ATCC 49226, and the fungi *Candida albicans* ATCC 90028 and *Cryptococcus neoformans* ATCC 90112, following established broth microdilution susceptibility assays. The minimum inhibitory concentration was defined as the lowest concentration of irciniastatin A that inhibited all visible growth of the test organism (optically clear). Assays were repeated on separate days. (National Committee for Clinical Laboratory Standards. Methods for Dilution Antimicrobial Susceptibility Tests for Bacteria that Grow Aerobically. Approved Standard M7-A5. Wayne, Pa.: NCCLS, 2000; National Committee for Clinical Laboratory Standards. Reference Method for Broth Dilution Antifungal Susceptibility Testing of Yeasts. Approved Standard M27-A. Wayne, Pa.: NCCLS, 1997.)

Administration

Dosages

The dosage of the presently disclosed compounds to be administered to humans and other animals requiring treatment will depend upon numerous factors, including the identity of the neoplastic disease; the type of host involved, including its age, health and weight; the kind of concurrent treatment, if any; the frequency of treatment and therapeutic ratio. Hereinafter are described various possible dosages and methods of administration, with the understanding that the following are intended to be illustrative only, and that the actual dosages to be administered, and methods of administration or delivery may vary therefrom. The proper dosages and administration forms and methods may be determined by one of skill in the art.

Illustratively, dosage levels of the administered active ingredients may be: intravenous, 0.1 to about 20 mg/kg; intramuscular, 1 to about 50 mg/kg; orally, 5 to about 100 mg/kg; intranasal instillation, 5 to about 100 mg/kg; and aerosol, 5 to about 100 mg/k of host body weight.

Expressed in terms of concentration, an active ingredient may be present in the compositions of the present invention for localized use about the cutis, intranasally, pharyngolaryngeally, bronchially, intravaginally, rectally, or ocularly in concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention may preferably be presented for administration to humans and animals in unit dosage forms, such as tablets, capsules, pills, powders, granules, suppositories, sterile parenteral solutions or suspensions, sterile non-parenteral solutions of suspensions, and oral solutions or suspensions and the like, containing suitable quantities of an active ingredient. Other dosage forms known in the art may be used.

For oral administration either solid or fluid unit dosage forms may be prepared.

Powders may be prepared by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules may be produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules may be prepared by machine encapsulation of a slurry of active ingredients with an acceptable vegetable oil, light liquid petrolatum or other inert oil or triglyceride.

Tablets may be made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously, the tablet may be provided with a protective coating consisting of a sealing coat or enteric coat of shellac, a coating of sugar and methylcellulose and polish coating of carnauba wax.

Fluid unit dosage forms for oral administration such as in syrups, elixirs and suspensions may be prepared wherein each teaspoonful of composition contains a predetermined amount of an active ingredient for administration.

The water-soluble forms may be dissolved in an aqueous vehicle together with sugar, flavoring agents and preservatives to form a syrup. An elixir is prepared by using a hydroalcoholic vehicle with suitable sweeteners together with a flavoring agent. Suspensions may be prepared of the insoluble forms with a suitable vehicle with the aid of a suspending agent such as acacia, tragacanth, methylcellulose and the like.

For parenteral administration, fluid unit dosage forms may be prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide or another method known to one of skill in the art before suspending in the sterile vehicle. Advantageously, a surfactant or wetting agent may be included in the composition to facilitate uniform distribution of the active ingredient.

In addition to oral and parenteral administration, the rectal and vaginal routes may be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal installation, a fluid unit dosage form may be prepared utilizing an active ingredient and a suitable pharmaceutical vehicle, preferably P.F. water, a dry powder, can be formulated when insulation is the administration of choice.

For use as aerosols, the active ingredients may be packaged in a pressurized aerosol container together with a gaseous or liquefied propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of potentially suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof. The notation "active ingredient" signifies the compounds described herein.

Composition "A"

Hard-Gelatin Capsules

One thousand two-piece hard gelatin capsules for oral use, each capsule containing 200 mg of an active ingredient are prepared from the following types and amounts of ingredients:

| | |
|---|---|
| Active ingredient, micronized | 20 g |
| Corn Starch | 20 g |
| Talc | 20 g |
| Magnesium stearate | 2 g |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing an active ingredient in 5, 25 and 50 mg amounts by substituting 5 g, 25 g and 50 g of an active ingredient for the 20 g used above.

Composition "B"

Soft Gelatin Capsules

One-piece soft gelatin capsules for oral use, each containing 20 mg of an active ingredient, finely divided by means of an air micronizer, are prepared by first suspending the compound in 0.5 ml of corn oil to render the material capsulatable and then encapsulating in the above manner.

The foregoing capsules are useful for treating a neoplastic disease by the oral administration of one or two capsules one to four times a day.

Composition "C"

Tablets

One thousand tablets, each containing 20 mg of an active ingredient, are prepared from the following types and amounts of ingredients:

| | |
|---|---|
| Active ingredient, micronized | 20 g |
| Lactose | 300 g |
| Corn starch | 50 g |
| Magnesium stearate | 4 g |
| Light liquid petrolatum | 5 g |

The active ingredient, finely divided by means of an air micronizer, is added to the other ingredients and then thoroughly mixed and slugged. The slugs are broken down by forcing them through a Number Sixteen screen. The resulting granules are then compressed into tablets, each tablet containing 20 mg of the active ingredient.

The foregoing tablets are useful for treating a neoplastic disease by the oral administration of one or two tablets one to four times a day.

Using the procedure above, tablets are similarly prepared containing an active ingredient in 25 mg and 10 mg amounts by substituting 25 g and 10 g of an active ingredient for the 20 g used above.

Composition "D"

Oral Suspension

One liter of an aqueous suspension for oral use, containing in each teaspoonful (5 ml) dose, 50 mg of an active ingredient, is prepared from the following types and amounts of ingredients:

| | |
|---|---|
| Active ingredient, micronized | 1 g |
| Citric acid | 2 g |
| Benzoic acid | 1 g |
| Sucrose | 790 g |
| Tragacanth | 5 g |
| Lemon Oil | 2 g |
| Deionized water, q.s. | 1000 ml |

The citric acid, benzoic acid, sucrose, tragacanth and lemon oil are dispersed in sufficient water to make 850 ml of suspension. The active ingredient, finely divided by means of an air micronizer, is stirred into the syrup unit uniformly distributed. Sufficient water is added to make 1000 ml.

The composition so prepared is useful for treating a neoplastic disease at a dose of 1 teaspoonful (15 ml) three times a day.

Composition "E"

Parenteral Product

A sterile aqueous suspension for parenteral injection, containing 3 mg of an active ingredient in each milliliter for treating a neoplastic disease, is prepared from the following types and amounts of ingredients:

| | |
|---|---|
| Active ingredient, micronized | 3 g |
| POLYSORBATE 80 | 5 g |
| Methylparaben | 2.5 g |
| Propylparaben | 0.17 g |
| Water for injection, q.s. | 1000 ml. |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1 ml) three times a day.

Composition "F"

Suppository, Rectal and Vaginal

One thousand suppositories, each weighing 2.5 g and containing 20 mg of an active ingredient are prepared from the following types and amounts of ingredients:

| | |
|---|---|
| Active ingredient, micronized | 1.5 g |
| Propylene glycol | 150 g |
| Polyethylene glycol #4000, q.s. | 2,500 g |

The active ingredient is finely divided by means of an air micronizer and added to the propylene glycol and the mixture passed through a colloid mill until uniformly dispersed. The polyethylene glycol is melted and the propylene glycol dispersion is added slowly with stirring. The suspension is poured into unchilled molds at 40° C. The composition is allowed to cool and solidify and then removed from the mold and each suppository foil wrapped.

The foregoing suppositories are inserted rectally or vaginally for treating a neoplastic disease.

Composition "G"

Intranasal Suspension

One liter of a sterile aqueous suspension for intranasal instillation, containing 2 mg of an active ingredient in each milliliter, is prepared from the following types and amounts of ingredients:

| | |
|---|---|
| Active ingredient, micronized | 1.5 g |
| POLYSORBATE 80 | 5 g |
| Methylparaben | 2.5 g |
| Propylparaben | 0.17 g |
| Deionized water, q.s. | 1000 ml. |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease, by intranasal instillation of 0.2 to 0.5 ml given one to four times per day.

An active ingredient can also be present in the undiluted pure form for use locally about the cutis, intranasally, pharyngolaryngeally, bronchially, or orally.

Composition "H"

Powder

Five grams of an active ingredient in bulk form is finely divided by means of an air micronizer. The micronized powder is placed in a shaker-type container.

The foregoing composition is useful for treating a neoplastic disease, at localized sites by applying a powder one to four times per day.

Composition "I"

Oral Powder

One hundred grams of an active ingredient in bulk form is finely divided by means of an air micronizer. The micronized powder is divided into individual doses of 20 mg and packaged. The foregoing powders are useful for treating a neoplastic disease, by the oral administration of one or two powders suspended in a glass of water, one to four times per day.

Composition "J"

Insulation

One hundred grams of an active ingredient in bulk form is finely divided by means of an air micronizer. The foregoing composition is useful for treating a neoplastic disease, by the inhalation of 30 mg one to four times a day.

It is of course understood that such modifications, alterations and adaptations as will readily occur to the artisan confronted with this disclosure are intended within the spirit of the present invention.

TABLE 1

The $^{13}$C- and $^1$H-NMR assignment (recorded in CDCl$_3$) for irciniastatin A (1) and irciniastatin B (2)

| | A (1) | | | | B (2) | | | |
|---|---|---|---|---|---|---|---|---|
| Carbon No. | $^1$H δ | J (Hz) | $^{13}$C δ | HMBC (from H to C) | Carbon No. | $^1$H δ | J (Hz) | $^{13}$C δ | HMBC (from H to C) |
| 1 | 4.80 s | | 113.06 t | 2, 3 | 1 | 4.80 s | | 113.07 t | 2, 3 |
| 2 | | | 141.96 s | | 2 | | | 141.89 s | |
| 3a | 2.18 m | | 37.58 t | 1, 2, 4, 5, 25 | 3a | 2.16 m | | 37.21 t | 1, 2, 4, 25 |
| 3b | 2.38 dd | 4.0, 15 | | 1, 2, 4, 5, 25 | 3b | 2.36 m | | | 1, 2, 4, 25 |
| 4 | 3.74 m | | 80.53 d | 3, 6, OCH$_3$ | 4 | 3.74 m | | 80.36 d | OCH$_3$ |
| OCH$_3$ | 3.38 s | | 57.92 q | 4 | OCH$_3$ | 3.36 s | | 56.41 q | |
| 5 | 4.11 d | 2.5 | 73.11 d | 3, 4, 6 | 5 | 4.44 d | 2.5 | 72.23 d | 3, 4, 6 |
| OH | 5.76 s$^a$ | | | | | | | | |
| 6 | | | 173.49 s | | 6 | | | 172.77 s | |
| NH | 7.09 d | 10.5 | | 6 | NH | 7.36 d | 10 | | 6 |
| 7 | 5.45 t | 4.5 | 78.31 d | 6, 8, OCH$_3$ | 7 | 5.20 t | 4.5 | 80.24 d | OCH$_3$ |
| OCH$_3$ | 3.38 s | | 56.25 q | 7 | OCH$_3$ | 3.38 s | | 56.67 q | |
| 8 | 3.89 m | | 73.11 d | 7, 12 | 8 | 3.89 m | | 73.58 d | 7, 10, 12 |
| 9a | 1.81 m | | 29.70 t | 7, 8, 10, 11 | 9 | 2.62 m | | 38.58 t | 7, 8, 10 |
| 9b | 2.06 m | | | 7, 8, 10, 11 | | | | | |
| 10 | 3.67 dd | 4.0, 10.5 | 71.41 d | 11, 12, 27 | 10 | | | 210.00 s | |
| 11 | | | 38.75 s | | 11 | | | 49.40 s | |
| 12 | 3.53 d | 10.5 | 81.90 d | 8, 10, 11, 13, 14, 26 | 12 | 4.00 d | 11 | 82.96 d | 8, 10, 11, 13, 26 |
| 13 | 1.62 m | | 32.11 t | 12 | 13 | 1.58 m | | 32.17 t | |
| 14 | 3.96 m | | 73.75 d | 12, 16, 26 | 14 | 4.08 m | | 72.40 d | 16 |
| OH | 4.36 s | | | 13, 14, 15 | | | | | |
| 15 | 1.84 m | | 42.62 d | 14, 16 | 15 | 1.90 m | | 42.64 d | |
| 16 | 4.53 m | | 79.41 d | 14, 15, 18, 26 | 16 | 4.57 m | | 80.09 d | |
| 17a | 2.82 m | | 28.39 t | 15, 16, 18, 19, 23 | 17a | 2.88 m | | 28.18 t | |
| 17b | 2.89 m | | | 16, 18, 19, 23 | | | | | |
| 18 | | | 139.68 s | | 18 | | | 139.69 s | |
| 19 | | | 113.20 s | | 19 | | | 113.07 s | |

TABLE 1-continued

The $^{13}$C- and $^1$H-NMR assignment (recorded in CDCl$_3$) for irciniastatin A (1) and irciniastatin B (2)

| | A (1) | | | | | B (2) | | | |
|---|---|---|---|---|---|---|---|---|---|
| Carbon No. | $^1$H δ | J (Hz) | $^{13}$C δ | HMBC (from H to C) | Carbon No. | $^1$H δ | J (Hz) | $^{13}$C δ | HMBC (from H to C) |
| 20 | | | 160.08 s | | 20 | | | 162.36 s | |
| OH | 4.60 s[a] | | | 21 | | | | | |
| 21 | 6.31 s | | 101.28 d | 19, 20, 22, 23, 24 | 21 | 6.32 s | | 101.37 d | |
| 22 | | | 162.29 s | | 22 | | | 162.36 s | |
| OH | 11.13 s | | | 21, 22, 23 | | | | | |
| 23 | | | 101.59 s | | 23 | | | 101.37 s | |
| 24 | | | 170.44 s | | 24 | | | 170.48 s | |
| 25 | 1.76 s | | 22.68 q | 1, 2, 3 | 25 | 1.75 s | | 22.66 q | 1, 2, 3 |
| 26 | 0.92 s | | 13.67 q | 11, 27 | 26 | 1.10 s | | 19.21 q | 10, 11, 27 |
| 27 | 0.97 s | | 23.06 q | 11, 26 | 27 | 1.16 s | | 22.16 q | 10, 11, 26 |
| 28 | 1.10 d | 6.0 | 9.36 q | 14, 16 | 28 | 1.11 d | | 9.02 q | 14, 15, 16 |
| 29 | 2.02 s | | 10.44 q | 17, 18, 19 | 29 | 2.08 s | | 10.53 q | 17, 18, 19 |

[a]The data were obtained using CD$_3$OH as solvent.

TABLE 2

Inhibition of cancer cell line growth (GI$_{50}$ µg/ml) by irciniastatins A (1) and B (2)

| Human Cancer | Cell Line | Irciniastatin A | Irciniastatin B |
|---|---|---|---|
| Pancreas | BXPC-3 | 0.0038 | 0.00073 |
| Breast | MCF-7 | 0.0032 | 0.00050 |
| CNS | SF268 | 0.0034 | 0.00066 |
| Lung | NCI-H460 | <0.0001 | 0.0012 |
| Colon | KM20L2 | 0.0027 | 0.0021 |
| Prostate | DU-145 | 0.0024 | 0.0016 |
| Leukemia[a] | P388 | 0.00413 | 0.006 |
| Normal Endothelial | HUVEC[b] | <0.0005 | ND |

[a]Murine
[b]BD-Biosciences Clontech

What we claim is:

1. An essentially pure compound having a structure as follows:

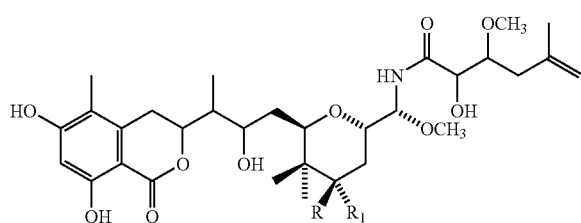

wherein R=OH and R$_1$=H.

2. An essentially pure compound having a structure as follows:

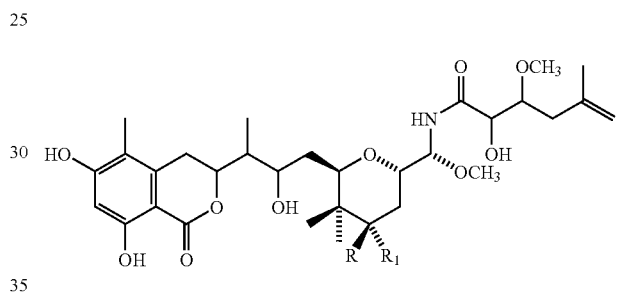

wherein R=R$_1$=O.

3. A pharmaceutical composition comprising the compound of claim 1.

4. A pharmaceutical composition comprising the compound of claim 2.

5. A method for treating cells or tissue afflicted with neoplastic disease, comprising administering an effective amount of the composition of claim 3.

6. A method for treating cells or tissue afflicted with neoplastic disease, comprising administering an effective amount of the composition of claim 4.

7. A method for treating humans and animals having cancer, comprising administering a pharmaceutically effective amount of the composition of claim 3.

8. A method for treating humans and animals having cancer, comprising administering a pharmaceutically effective amount of the composition of claim 4.

* * * * *